United States Patent [19]

Bruno

[11] Patent Number: 5,020,665

[45] Date of Patent: Jun. 4, 1991

[54] STORAGE/CARRYING DEVICES FOR TRANSPORT OF HYPODERMIC NEEDLE/SYRINGE ASSEMBLIES TO BEDSIDE USE AND ULTIMATE DISPOSAL

[76] Inventor: John Bruno, 77-83 Second Ave., Paterson, N.J. 07514

[21] Appl. No.: 496,857

[22] Filed: Mar. 21, 1990

Related U.S. Application Data

[62] Division of Ser. No. 214,332, Jul. 1, 1988.

[51] Int. Cl.$^5$ .............................................. B65D 83/10
[52] U.S. Cl. .................................... 206/366; 206/363; 206/364; 206/365; 206/370; 206/561; 220/555; 220/94 A; 220/23.8
[58] Field of Search ............... 206/363, 364, 365, 366, 206/370, 372, 373, 558, 561, 562, 563; 220/21, 23.8, 23.83, 94 A, 505, 553, 555

[56] References Cited

U.S. PATENT DOCUMENTS

| D. 169,433 | 8/1953 | Goldman | 206/562 |
|---|---|---|---|
| 3,618,749 | 11/1971 | Valcaro | 206/372 |
| 3,820,656 | 6/1974 | Orr | 206/558 |
| 4,170,300 | 10/1979 | Pick | 206/365 |
| 4,550,828 | 11/1985 | Baldwin et al. | 206/372 |
| 4,613,041 | 9/1986 | Carlton | 206/373 |

*Primary Examiner*—David T. Fidei
*Attorney, Agent, or Firm*—Morgan & Finnegan

[57] ABSTRACT

A storage/carrying device for safely and conveniently transporting to a patient's bedside sterile needle and syringe devices used in medication and blood collection procedures, and, additionally, to safely transport such implements to ultimate disposal after use, substantially without risk of contaminating contact with the storage/carrying device, or injury or infection to the person handling the device. The storage/carrying device is formed as an integral, unitary assembly comprising first and second transport wells, an extension transport well, a pair of carrying trays, and a carrying handle. The first transport well is adapted to securely store used intravenous-type needles, including the plastic tubing attached to such needles, for transport to ultimate disposal, and can be further adapted to similarly store the syringe portions of used needle/syringe assemblies. The second transport well is proportioned to safely store and transport sterile needle/syringe assemblies pre-filled with medication, or to be used for blood collection, such that the safety-capped needle ends thereof can rest along the bottom of the well. Each carrying tray is proportioned to retain two standard one-ounce medication cups. One of the trays provides a slot through an upstanding sidewall portion thereof dimensioned to retain the handle of a pair of scissors such that the scissor blades can safely rest along the bottom of the tray. The extension transport well is adapted to retain a tubular storage/containment device therewithin for safely removing needles from used hypodermic needle/syringe assemblies, or, alternatively, a tubular container adapted to transport used needle/syringe assemblies in-tact, as well as a needle/collection tube holder assembly used in vacuum-tube blood collection procedures. The tubular container can be further adapted for use independent of the storage/carrying device.

29 Claims, 6 Drawing Sheets

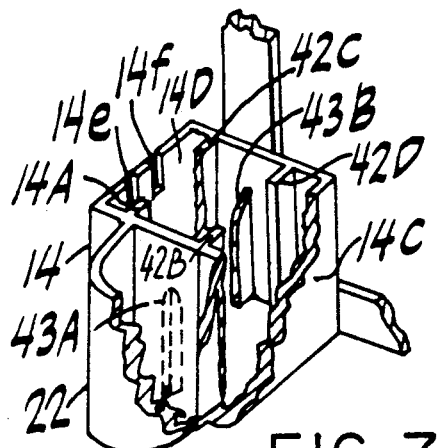
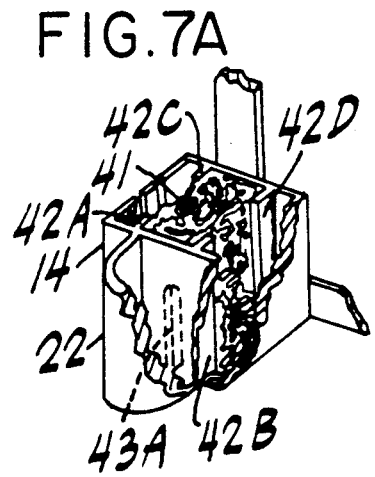
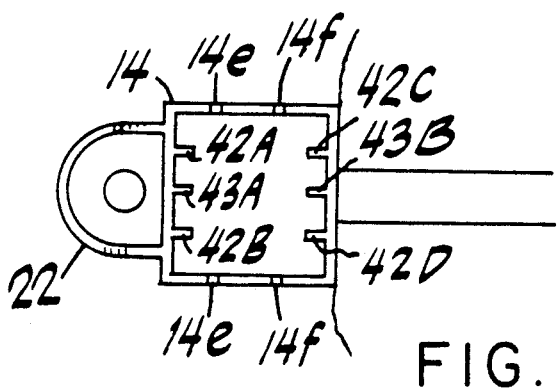
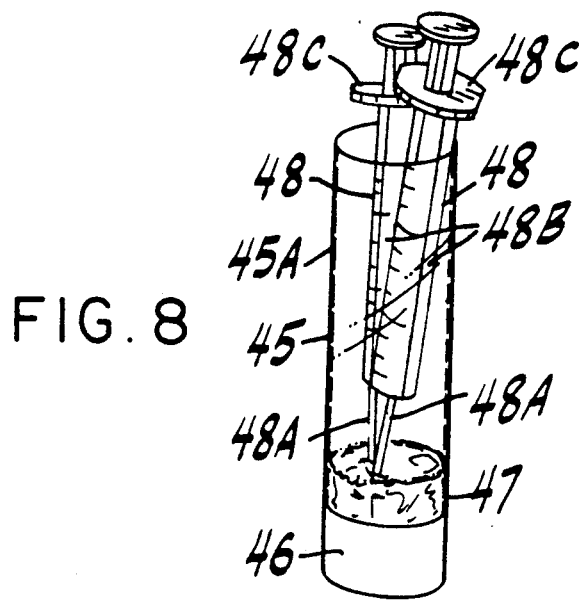

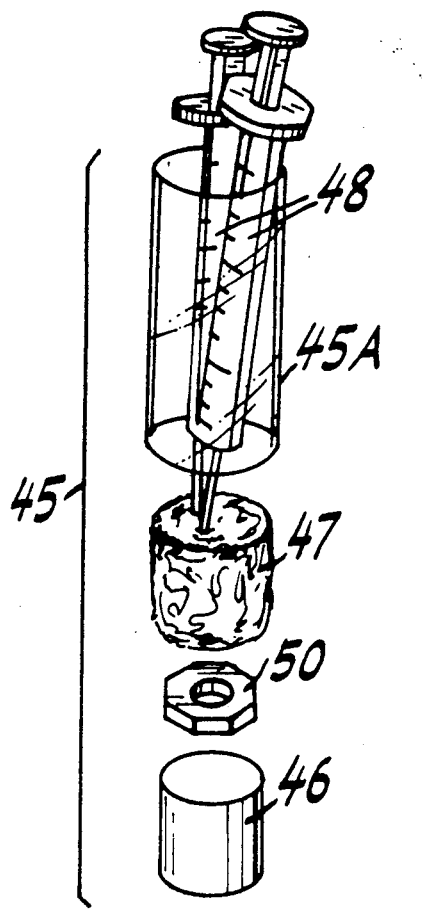
FIG. 9A
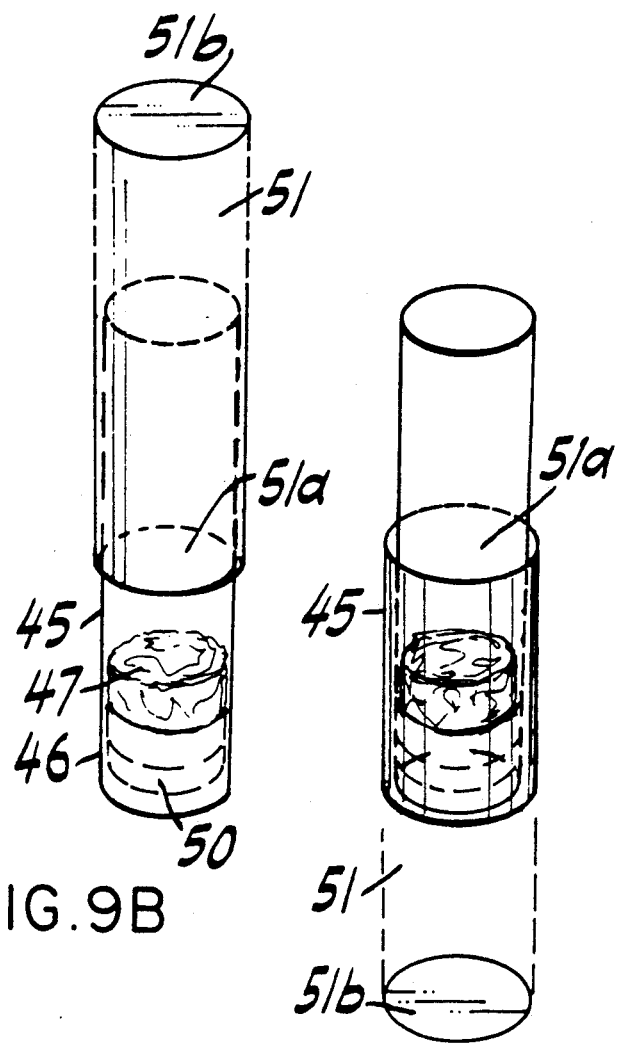
FIG. 9B
FIG. 9C

STORAGE/CARRYING DEVICES FOR TRANSPORT OF HYPODERMIC NEEDLE/SYRINGE ASSEMBLIES TO BEDSIDE USE AND ULTIMATE DISPOSAL

This is a divisional of co-pending application Ser. No. 07/214,332 filed July 1, 1988.

BACKGROUND AND OBJECTS OF THE INVENTION

The present invention relates generally to devices which facilitate bedside infection control in hospitals, and, more particularly, to a storage/carrying device which provides for safe and convenient transport to a patient's bedside of sterile needle/syringe assemblies typically used in medication and blood collection procedures, and, additionally, provides for safe transport to ultimate disposal of such needles and syringes after use, substantially without risk of contaminating contact with the storage/carrying device or the person handling it.

With the widespread use of disposable medical implements, particularly hypodermic needles and syringes, a definite need has developed for ways to safely and conveniently handle and transport such implements to the site of their use, and, to dispose of such implements after use without risk of exposing any person handling them to injury, infection or disease by puncture or contact with a used needle or syringe. The tragic outbreak of the highly contagious AIDS disease has dramatically highlighted the need for safer handling, storage and disposal of such implements.

In today's hospitals, a wide variety of disposable needle and syringe devices are routinely used to administer medication by injection and intravenous ("I.V.") procedures, and for intravenous blood collection. For the typical injection procedure, the nurse or medical technician will pre-fill a sterile needle/syringe assembly with medication at the nurses' station or at a medication cart outside the patient's room. During blood collection procedures, the nurse will either prepare a sterile needle/syringe assembly to draw blood for immediate transfer to a vacuum tube-type collection device, or draw the blood directly into the collector by means of a multi-sample needle/collection tube holder device. For I.V. medication procedures, a butterfly or other intravenous-type needle attachment, which includes a plastic tubing connection, will be attached to an I.V. bag for intravenous, controlled gravity feed of medication to the patient.

Invariably, the nurse will carry the appropriate needles and/or syringes by hand or in a uniform pocket to the patient's beside along with other items normally attendant to an injection, blood collection, or I.V. procedure, such as gauze material, alcohol preps, and bandages. This often presents an unwieldy situation for the nurse who is forced to manually handle multiple items on route to the patient's bedside and while preparing the patient for the injection or venepuncture, thus increasing the risk of dropping or otherwise mishandling the needle or syringe and exposing it to contamination.

Disposal of such needle and syringe devices after use presents potentially more serious difficulties. Once an injection is given, a blood sample drawn, or an I.V. needle removed from a patient, both the needle and/or syringe used in the procedure is contaminated and must be disposed of in a safe manner. It had once been common practice to break or cut the needle after use before transport to ultimate disposal in order to eliminate the sharp end point so as to reduce the risk of puncture, scratching or other injury which might result from handling. In breaking or cutting the needles, however, a substantial danger existed that accidental puncture might occur during the breaking or cutting operations, thus exposing the holder to possible injury and, further, to possible infection or disease as a result of such puncture. In addition, residual medication or blood in the needle or the syringe can splatter onto the person or his clothes, and, potentially harmful fumes from the residual medication could be inhaled as a result of the so-called aerosol effect. Furthermore, the blades of the cutting tool are now recognized as a breeding ground for germs, bacteria and other disease-causing microorganisms to which an unsuspecting person cutting the needle could be unnecessarily exposed.

Recently, an even greater danger has been recognized in connection with the handling and disposal of used needles as well as other sharp medical implements. It is now recognized that certain diseases, most notably Hepatitis B, can be transmitted by covert percutaneous—i.e., by merely contacting the contaminated needle or implement.

As a result of the foregoing dangers, it is preferred current practice to dispose of such devices in-tact, without dismantling them. However, in disposing of the whole hypodermic needle and syringe, the used needle has sometimes been recapped before disposal with the same protective sheath that was used during shipment from the manufacturer. The resheathing was intended to prevent possible injury while a person carries the needle to a suitable disposal unit. This practice itself, however, can result in accidental puncture or contact while the needles point is being resheathed. Because of this danger it is now recommended by the Center For Disease Control ("C.D.C.") that needles not be resheathed after use.

In this regard, the C.D.C. has been strongly urging hospitals to provide in-room receptacles for disposal of used needle/syringe assemblies in-tact, without recapping the needle. While such disposal devices have been generally satisfactory, they may still have a few shortcomings. In-room disposal devices can be costly and require permanent installation in a patient's room. Moreover, in-room receptacles may not eliminate the inherent risk of contaminating contact or accidental puncture associated with the manual transport of an exposed used needle/syringe assembly even a short distance from the patient's bedside.

Most importantly, the nurse, as a practical matter, almost always has important duties to perform immediately after giving an injection or drawing blood (such as treating the injected area, covering the exposed patient, etc.) which makes walking to a receptacle to dispose of a used needle a lesser priority, and thereby increases the risk of an exposed needle being left on a nearby table or even on the patient's bed. This could be particularly hazardous in the case of medical personnel who leave used needle/syringe assemblies unattended in a psychiatric patient's room for even a few seconds while attending to other duties within or without the patient's room.

Additionally, there may be instances where a disposal device for the whole needle/syringe assembly is not desired. For example, in emergency rooms, the urgency of a particular emergency situation may not permit time to seek out an appropriate disposal unit for the used needle/syringe assembly. In the absence of an immediately available disposal device it is likely that the used needle could be left lying unattended and unsecured, or an attempt might be made to resheath the needle. In either event, there are substantial risks of accidental puncture by or contact with contaminated needles.

In order to overcome such difficulties, various approaches have been advanced for removal of the needle from its syringe after use and safely storing it for ultimate disposal (see, e.g., the storage/containment device disclosed in Applicant's pending application Ser. No. 07/012,949 filed Feb. 10, 1987). While the used needle presents the most significant risk of injury or infection through accidental puncture or scratching of a person's skin, the used syringe may also present a risk of infection. For example, a used syringe can contain residual blood or medication which, if exposed to a person's skin, may be absorbed topically (particularly if a cut or break is present) and may cause a serious internal infection or other reaction. Thus, even where such a needle removal and storage device is employed, the used syringe will still require independent, safe disposal.

Accordingly, it is an object of the present invention to provide a new storage/carrying device which can be economically fabricated, and which is of a durable yet lightweight construction, for conveniently and safely storing and transporting sterile needle/syringe assemblies to a patient's bedside for use in medication and blood collection procedures, thus eliminating the burden on the nurse to manually carry these implements to the patient's bedside and the associated risk of accidentally dropping them or otherwise exposing them to contamination.

It is also an object of the invention to provide a new storage/carrying device for conveniently and safely storing and transporting used hypodermic needles and syringes, as well as butterfly or other intravenous-type needle assemblies, to ultimate disposal without risk of contaminating contact with the device, or of exposing the person handling the device to injury, infection or disease by puncture or contact with the used needle or syringe.

It is a further object of the present invention to provide a new storage/carrying device for conveniently and safely storing and transporting used needle/syringe assemblies to ultimate disposal, in-tact, thus eliminating both the need for potentially costly in-room disposal receptacles, and the risk of accidental puncture or contact with a contaminated needle inherent during manual transport to such disposal devices.

It is yet another object of the present invention to provide a new storage/carrying device for storing and transporting used needles and syringes to ultimate disposal which is compact in size so as to be easily locked inside a standard hospital medication cart when unattended, thus obviating the risks caused by leaving unattended receptacles in patients' rooms.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a hand-held, storage/carrying device for safely and conveniently transporting to a patient's bedside sterile needle/syringe assemblies prepared for injection and blood collection procedures without the nurse or other medical personnel having to hand-carry them, and, additionally, for safely transporting such needles and syringes to ultimate disposal after use, substantially without risk of contaminating contact with the device, or of exposing the person carrying the device to injury, infection, or disease by puncture or contact with a used needle or syringe.

The storage/carrying device comprises a generally square first transport well, a generally U-shaped cylindrical second transport well, a pair of carrying trays, an extension transport well, and a carrying handle, all integrated into a unitary assembly. The carrying handle comprises a grasping portion disposed above the first and second transport wells and a pair of leg members integrated with the grasping portion at opposite ends thereof and extending downwardly therefrom. Advantageously, one leg member is integrally molded to an attaching sidewall of the first transport well and the other leg member is molded to a flat sidewall portion of the second transport well to provide enhanced structural integrity to the storage/carrying device.

According to one specific aspect of the invention, the first transport well is proportioned to closely receive and retain a one-ounce plastic medication cup for storage and transport to ultimate disposal of syringes removed from used needle/syringe assemblies. Advantageously, the sidewalls of the first transport well are dimensioned to a height sufficient to substantially reduce the risk of the medication cup tipping over under the weight of the used syringes and the implements falling out of the well. Also advantageously, the first transport well is provided with a plurality of engaging slots formed through the top edge of each of two sidewalls thereof. Each engaging slot is proportioned such that the portions of the sidewall defining the slot will frictionally engage the plastic tubing attached to a butterfly or other intravenous-type needle. With the tubing securely engaged in one of the slots, the needle can be placed in the plastic cup for safe transport to ultimate disposal after use without risk of contaminating contact with the storage/carrying device or injury or infection to the person handling the device.

According to another aspect of the invention, the second transport well is adapted to safely store and transport to a patient's bedside sterile syringe/needle assemblies used in medication and blood collection procedures such that the safety-capped needle end of the implement can rest along the bottom of the well. As preferably embodied, the second transport well is proportioned to a depth approximately 1.5 times greater than that of the first transport well so as to accommodate two 60 millileter needle/syringe assemblies, but can be proportioned to accommodate various sizes and quantities of such implements as desired for a given injection or blood collection procedure.

In accordance with the invention, the extension transport well is formed in a generally U-shaped cylindrical configuration and has a common sidewall with the first transport well. The extension well is proportioned to a depth approximately equal to that of the first transport well, and is adapted to frictionally engage the containment member of the storage/containment device for safely removing needles from hypodermic needle/syringe assemblies disclosed in Applicant's pending application Ser. No. 07/012,949, filed Feb. 10, 1987. In an alternate embodiment of the invention, the extension well is removed from the storage/carrying device and the depth of the first transport well is increased to approximately the same depth as the second transport well to facilitate safe storage and transport of entire used needle/syringe assemblies, in-tact.

According to still another specific aspect of the invention, the storage/carrying device is provided with a pair of carrying trays disposed on opposite sides of the grasping portion of the carrying handle. Each tray comprises a first upstanding sidewall connected to the sidewalls of the first and second transport wells which are molded to the leg members of the carrying handle. Further, each tray is provided with a curved base portion extending outwardly in perpendicular with the bottom edge of the first sidewall To complete each tray, a second, curved sidewall is formed around the outwardly extending edges of the base portion The second sidewall is attached to both the first sidewall of the tray at its engagement with the first transport well and the U-shaped sidewall of the second transport well.

As preferably embodied, each tray is proportioned to securely retain two one-ounce medication cups and can store items normally attendant to an injection, I.V., or blood collection procedure, such as gauze material, alcohol preps, and bandages, thus obviating the nurse's normal cumbersome practice of carrying such items by hand or in a uniform pocket to a patient's bedside. Advantageously, one of the trays is further provided with a scissor-retaining slot formed through the curved sidewall thereof at its abutment with the U-shaped sidewall of the second transport well. The slot is proportioned to receive and retain the handle portion of a pair of scissors such that the blades thereof can rest along the base portion of the tray.

According to the most preferred embodiment of the invention regarding the transport means for used I.V. needles and needle/syringe assemblies, the first transport well is adapted to house a needle engaging element formed from a foam-type material which is resilient, yet sufficiently rigid enough, so that the needle portions of used I.V. needle assemblies may be securely inserted thereinto for transport to disposal, yet easily removed therefrom at the disposal site. The element is dimensioned and positioned within the first transport well so as not to interfere with the use of the engaging slots formed in the sidewalls of the transport well to frictionally hold the tubing connection attached to the used I.V. needles.

According to another aspect of this most preferred embodiment of the invention, the extension transport well is adapted to frictionally retain a re-usable, open-ended tubular container adapted to transport to disposal a plurality of used needle/syringe assemblies in-tact, as well as the used needle portion of a multi-sample needle/collection tube holder assembly used in vacuum-tube blood collection procedures. The container is provided with a needle engaging insert at the bottom thereof made from a sponge rubber or plastic-type material into which the needle portions of the used devices can be fixedly inserted so as to provide greater resistance to movement of the devices during transport, and into which residual blood or medication in the needles can drain and be absorbed. As preferably embodied, the container is proportioned such that when a used needle/syringe assembly or needle/collection tube holder assembly is inserted thereinto, needle end first, the finger grips of the syringe or a sufficient portion of the collection tube holder will be exposed above the container sidewall so as to enable the user to pull the used implement out of the container at the disposal site substantially without risk of contaminating contact with the interior sidewall of the container.

According to still another aspect of the invention, the aforesaid tubular container is adaptable for use without the storage/carrying device. For such applications, the container, as preferably embodied, is further provided with a weighted metal insert fixedly sandwiched between the needle engaging insert and the bottom of the container to give added weight to the container. The added upright stability provided by the metal insert enables a person who must give an injection or take a blood sample to place the container on a flat surface and easily insert a used needle/syringe assembly or needle/collection tube holder assembly thereinto with one hand, substantially without fear of tipping the container over. Additionally, the container is provided with a tubular sleeve member formed with an open end and a closed end. The sleeve is proportioned to slidably fit over the top of the container and frictionally engage the container sidewall to securely enclose the used implements for transport to disposal. The sleeve is also slidably engagable with the container from the bottom end thereof so as to be securely retained with the container while in use.

It will be appreciated by those skilled in the art that this embodiment of the tubular container of the present invention is particularly useful for situations wherein it is desirable for the user to keep such used implements on his or her person—e.g., while attending to a psychiatric patient who may harm himself or anyone else present in his room with an unattended exposed needle.

It will be further appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

FIGS. 7A is a perspective view of the intravenous needle disposal means shown in FIG. 6.

FIGS. 7B and 7C are perspective and plan views, respectively, of the transport compartment for the intravenous needle disposal means shown in FIG. 6.

FIG. 8 is a front view of the used needle/syringe transport means shown in FIG. 6.

FIGS. 9A through 9C are frontal elevation views of the used needle transport means shown in FIG. 6 for use independent of the storage/carrying device of FIG. 6.

DETAILED DESCRIPTION OF PREFERRED EMBODIMENTS

Figure 1:
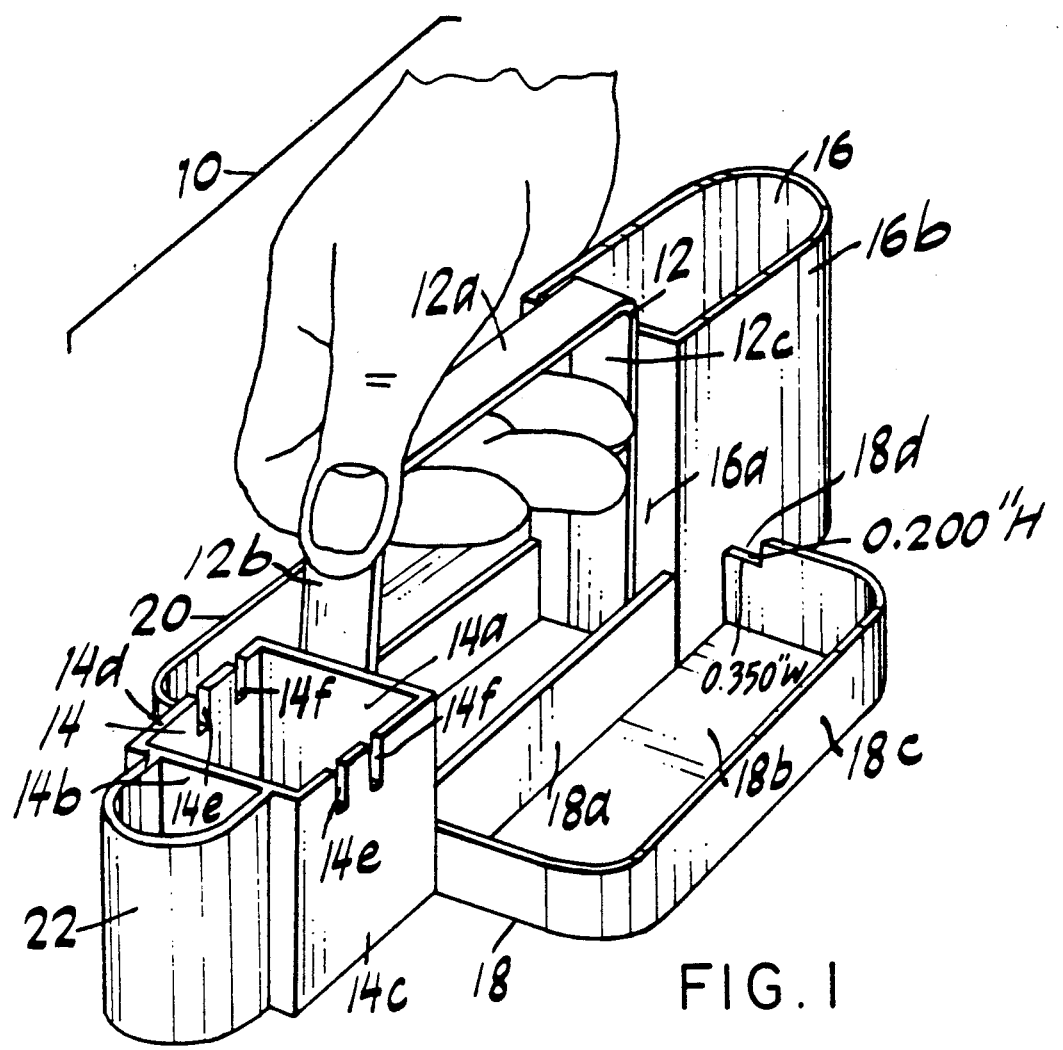
FIG. 1 is a perspective view of a preferred embodiment of the medical supply storage/carrying device according to the present invention.
Figure 2:
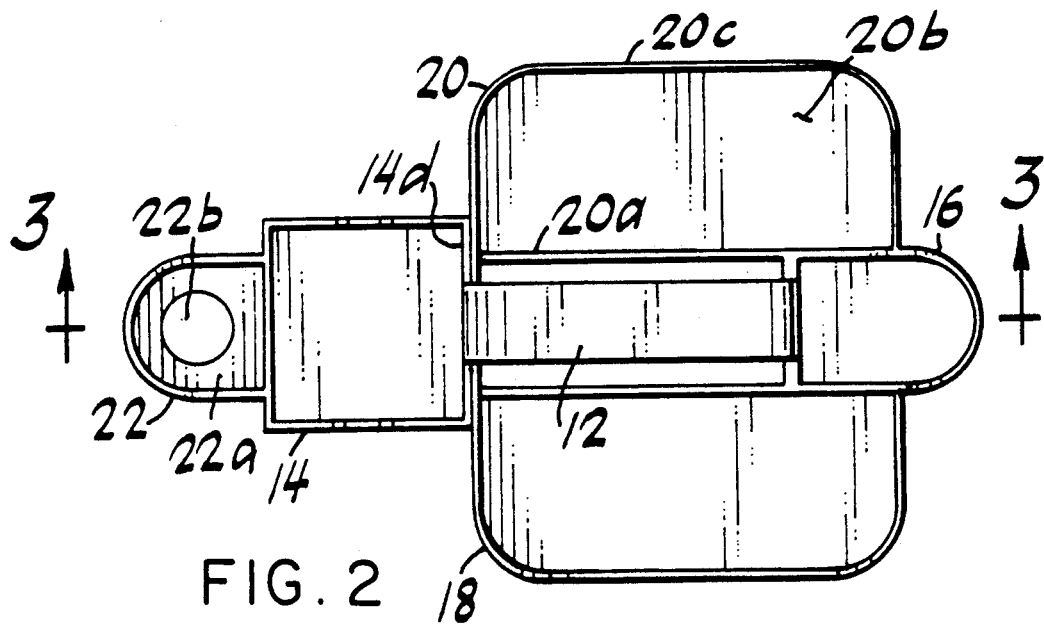
FIG. 2 is a top plan view of the medical supply storage/carrying device shown in FIG. 1.
Figure 3:
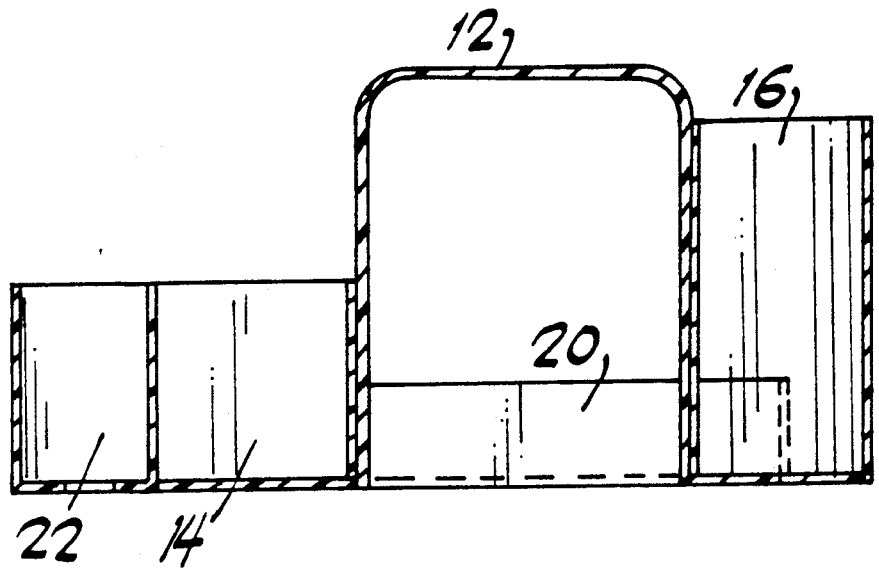
FIG. 3 is a sectional view taken along line 3—3 of the medical supply storage/carrying device shown in FIG. 2.

Referring now to the accompanying drawings wherein like reference characters refer to like parts throughout the various views, there is shown in FIGS. 1-4 a preferred embodiment of the medical supply storage/carrying device (indicated generally at 10) according to the present invention.

As here embodied, the storage/carrying device comprises a carrying handle 12, transport wells 14 and 16, a pair of carrying trays (18, 20), and an extension transport well 22, all integrated into a unitary assembly as more fully described below. Advantageously, the component parts of the storage/carrying device are made from an injection moldable, thermo-plastic material to ensure both durability and lightweight fabrication for ease of handling by the user. Moreover, the storage/carrying device is manufactured to an economically and functionally compact size (with an overall length of no more than approximately 8.5 inches, a height of about 4 inches, and an overall width of approximately 5 inches) such that the device can be safely and conveniently transported, and stored in a standard medication cart when left unattended.

According to the invention, carrying handle 12 is formed in a generally inverted U-shaped configuration and comprises a grasping portion 12a disposed higher than wells 14 and 16 and proportioned so as to substantially bridge the distance therebetween, integrated with an opposed pair of downwardly extending leg members 12b and 12c. As here embodied, leg members 12b and 12c are integrally molded along the entire height of sidewall 14a of transport well 14 and sidewall 16a of transport well 16, respectively. It will be understood that handle 12 may be fashioned in other configurations to facilitate secure handling and carrying of the storage/carrying device. For example, as more fully described below with respect to FIG. 5, the leg members may be shortened and molded to the top edges of sidewalls 14a and 16a rather than to the sidewalls themselves.

As preferably embodied, the storage/carrying device is provided with a transport well 14 formed in a generally square configuration from upstanding sidewalls 14a-14d. The interior of transport well 14 is proportioned to retain a standard one-ounce disposable medication cup (shown as reference character 30), within which syringes disassembled from used syringe/needle assemblies can be safely stored, and residual blood or liquid which may remain in a syringe collected, for transport to final disposal without the risk of contaminating contact with the storage/carrying device or the person handling it.

Preferably, the interior of transport well 14 is dimensioned to a length, width, and depth to closely receive cup 30 and provide sufficient sidewall height so as to substantially reduce the risk of the cup tipping over under the weight of a used syringe, and the syringe falling out of the transport well. For example, for a standard one-ounce medication cup, the length, width, and height of well 14 may each be 2.0 inches. Also advantageously, transport well 14 is provided with a pair of engaging slots (14e and 14f) formed through the upper edge of both upstanding sidewalls 14c and 14d. Each engaging slot is proportioned such that the portions of sidewalls 14e or 14f defining the slot will frictionally engage the plastic tubing affixed to a butterfly or other intravenous-type needle assembly (not shown), and which generally accompanies its removal from an I.V. apparatus after use. With the tubing securely engaged in one of the slots 14e or 14f, the used needle can be placed in cup 30 and safely transported to disposal without risk of contacting the storage/carrying device or the person handling it.

As here embodied, the storage/carrying device is also provided with a transport well 16 formed in a generally U-shaped configuration from a generally flat sidewall portion 16a integrated with a U-shaped sidewall 16b. The interior of transport well 16 is proportioned to receive and safely retain sterile needle/syringe assemblies pre-filled with medication or prepared for a blood collection procedure, such that the safety-capped needle ends thereof can rest on the bottom of the well with the syringes leaning against U-shaped sidewall 16a. As preferably embodied, the interior of transport well 16 is dimensioned to securely store two 60 millileter sterile needle/syringe assemblies (shown in FIG. 4 as reference characters 32) substantially without risk of their falling out of the well during transport (e.g., a depth of 3.5 inches, a width of 1.25 inches, and a length of 1.75 inches). It will be understood by those skilled in the art, however, that needle/syringe assemblies sold commercially for various medical applications come in a wide range of sizes (most ranging from 1 millileter to 60 millileters), and that transport well 16 can be proportioned accordingly to accommodate different sizes and quantities of such implements as desired.

According to the invention, a generally U-shaped cylindrical extension well member 22 is formed integrally with transport well 14 so as to have a common sidewall 14b therewith. The interior of extension well 22 is adapted to receive and frictionally retain the tubular storage/containment member (indicated by reference numeral 34a) of a containment device for safely removing and storing needles from hypodermic needle/syringe assemblies (indicated by reference character 34) of the type disclosed in the aforesaid pending application Ser. No. 07/012,949. Advantageously, because extension well 22 is designed for a frictional engagement with member 34a, the floor of the well (indicated by reference character 22a) is formed with a circular opening 22b as a means to reduce fabrication costs. After a needle is removed from a used needle/syringe assembly and stored in containment device 34, the used syringe can be stored in plastic cup 30 within transport well 14, as discussed above, and taken to disposal.

As preferably embodied, storage/carrying device 10 is further provided with a pair of carrying trays (18, 20) disposed on opposite sides of handle 12. Carrying trays 18 and 20 are each provided with a first upstanding sidewall (18a, 20a) integrally molded with both sidewall 14a of transport well 14 and sidewall 16a of transport well 16 so as to bridge the distance therebetween and provide enhanced structural integrity to the storage/carrying device. The carrying trays are each further provided with a generally curved base portion (18b, 20b), formed in an elongated U-shaped configuration, which extends outwardly from the bottom edge of the first upstanding sidewall in substantially perpendicular placement thereto. To complete each tray, a second, generally curved upstanding sidewall (18c, 20c) is formed around the edges of the base portion which extend outwardly from the first sidewall. As here embodied, each second sidewall is integrated with transport well 14 along a portion of sidewall 14a and connects its respective first sidewall (18a or 20a) at the first sidewall's engagement with sidewall 14a. Each second sidewall is further connected to transport well 16 at cylindrical sidewall 16b.

Figure 4:
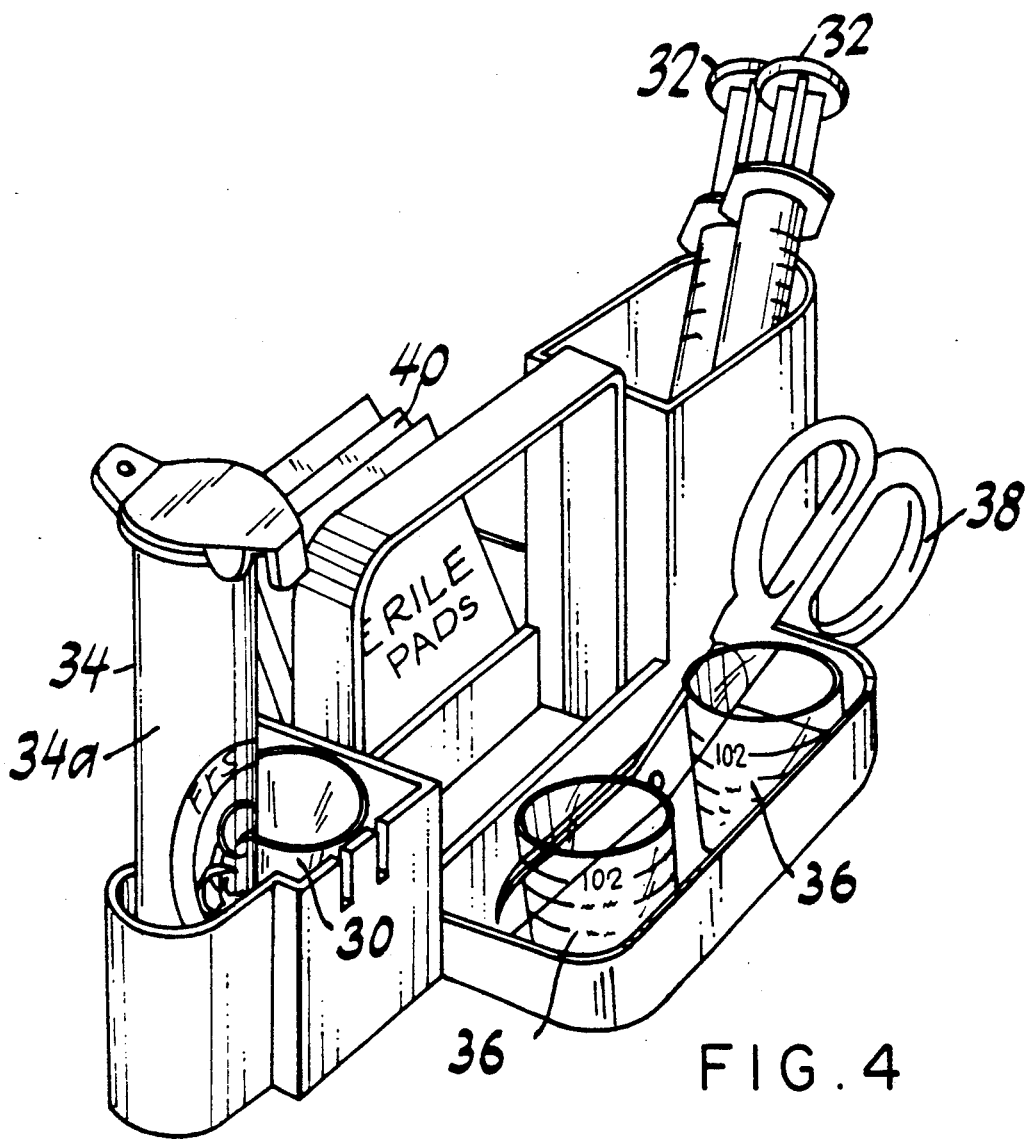
FIG. 4 is a perspective view of a preferred embodiment of the medical supply storage/carrying device according to the present invention showing the arrangement therein of various medical supplies intended for use with the device.

Advantageously, each carrying tray is proportioned to receive and retain two standard one-ounce plastic medication cups (indicated by reference character 36 on FIG. 4). Thus, as here embodied, sidewalls 18c and 20c are each dimensioned to a height of 1.0 inch to substantially reduce the risk of the medication cups tipping over or falling out of the trays during transport, and to securely store within the trays items such as sterile pads (indicated at reference numeral 40), gauze material and bandages, which may be required during the administration of an injection, I.V., or blood collection procedure. In accordance with the invention, second sidewall 18c is formed with a retaining slot 18d at its abutment with sidewall 16b. Slot lsd is proportioned to slidably receive and retain the handle of a pair of scissors which may be placed in the tray such that the blades thereof rest along the length of base 18b. As here embodied, slot 18d is dimensioned to a width of 0.350 inches and a height of 0.200 inches. It will be understood, however, that slot 18d may be dimensioned as desired to accommodate a variety of differently sized scissors.

Figure 5:
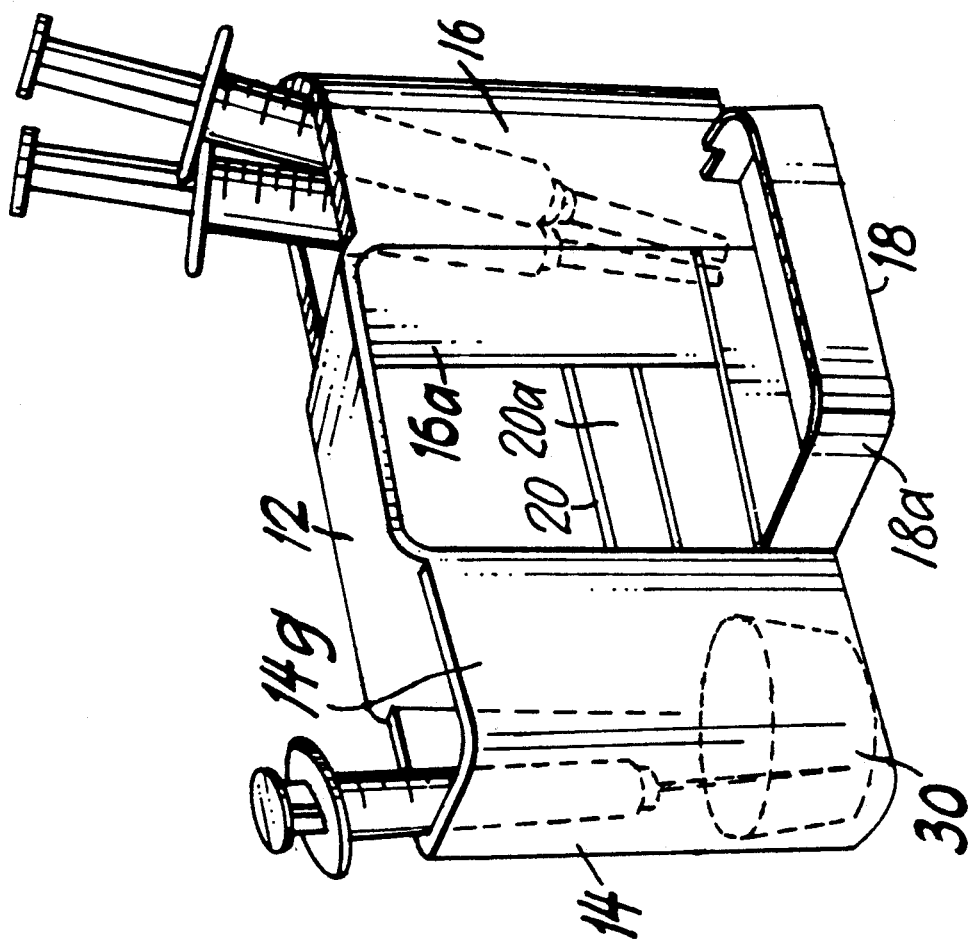
FIG. 5 is a perspective view of an alternative embodiment of the storage/carrying device according to the present invention.

In an alternative embodiment of the invention shown in FIG. 5, the storage/carrying device can be modified for applications wherein it is desired to store and transport entire used needle/syringe assemblies to ultimate disposal, without first removing the needles from the syringes. As here embodied, extension well 22 is eliminated from the storage/carrying device, and the depth of transport well 14 is increased to approximately the same depth as transport well 16 so as to securely store a plurality of used needle/syringe assemblies therein, in-tact, with the unsheathed needle end resting on the bottom of cup 30. In accordance with this embodiment of the invention, the storage/carrying device is fabricated so that carrying handle 12 comprises only a grasping portion which is formed integrally with the upper edges of sidewalls 14a and 16a of transport wells 14 and 16, respectively, and proportioned to approximately the same width as the sidewalls. Advantageously, transport well 14 is formed with a generally U-shaped, continuous sidewall 14g against which the syringe portions of the used needle/syringe assemblies can be leaned during transport.

Normal use of the medical supply storage/carrying device is relatively straightforward. For an injection or blood collection procedure, the appropriate medical personnel will prepare one or more sterile needle/syringe assemblies at the nurses, station or at the medication cart outside the patient's room and place them in transport well 16 with the capped needle ends resting on the bottom of the well. Gauze material, bandages, and alcohol preps are placed in carrying trays 18 and 20. Containment device 34 is slidably inserted into extension well 22 via tubular member 34a for post-procedure removal of the used needle. If a pair of scissors is required, they can be placed in tray 18 with the scissor blades resting along base 18c and the handle secured in notch 18d. With the aforementioned items thusly in place, the storage/carrying device can be grasped along handle 12 and conveniently hand-carried directly to the patient's bedside substantially without risk of exposing the items to contamination.

After blood is drawn from or an injection administered to a patient, and the used needle has been removed from the syringe using device 34, the syringe is placed in transport well 14 for disposal with the open end thereof resting on the bottom of plastic cup 30 so that any residual medication or blood remaining in the syringe can drain into the cup. Where the needle is not first removed from the syringe prior to disposal, as in the case where the embodiment of the present invention shown in FIG. 5 is used, the entire assembly can be placed in well 14 with the unsheathed used needle resting at the bottom of cup 30 essentially free from contaminating contact with the storage/carrying device or the person handling it. If an intravenous-type needle is to be disengaged for disposal from an intravenous assembly, the tubing attached to the needle is press-fit into one of the slots (14e or 14f) formed in the sidewalls (14c or 14d) of well 14 with the needle placed into cup 30.

Thus, with the appropriate used implements secured within storage/carrying device 10, the device can be stored in the medication cart for use in other procedures, or carried to the disposal site where the used implements can be ultimately disposed of. It will be appreciated by those skilled in the art that the safe storage and convenient transport means for sterile needle/syringe assemblies and used needles and syringes provided by the present invention greatly facilitates the needs of a busy hospital floor wherein several patients may require medication or their blood drawn within a prescribed period of time.

Figure 6:
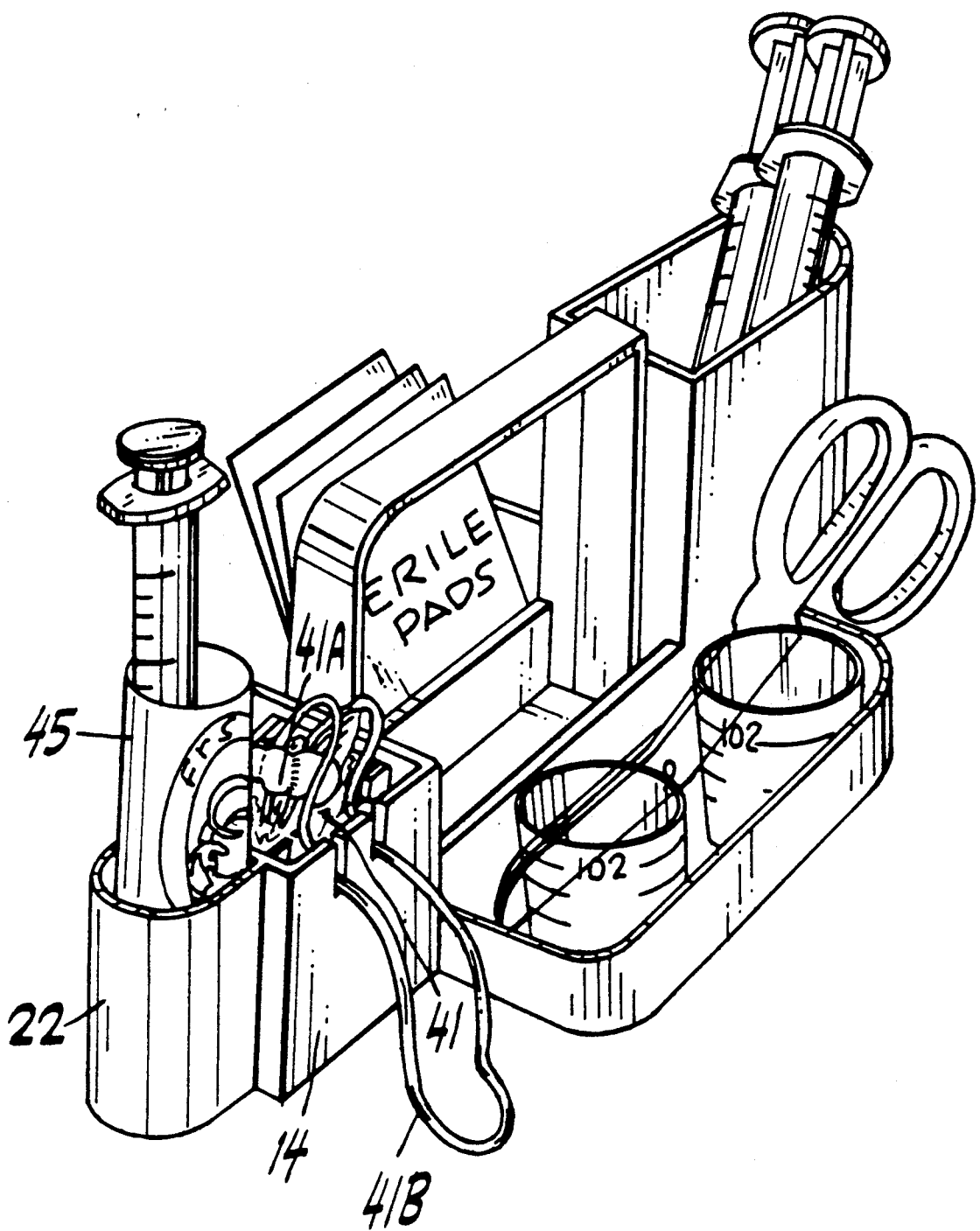
FIG. 6 is a perspective view of the preferred embodiment of the storage/carrying device of the present invention with respect to the means for transporting to disposal used needle/syringe assemblies, intravenous needles and the used needle portions of multi-sample needle/collection tube holder assemblies.

FIGS. 6 through 8 disclose the most preferred embodiment of the present invention with regard to the means for transporting used multi-sample blood collection needles, needle/syringe assemblies, and intravenous-type needles to ultimate disposal. As preferably embodied, transport well 14 is provided with a generally rectangular needle engaging element 41 adapted to fixedly engage the needle portions of used I.V. needle assemblies (shown as 41a in FIG. 6) for transport to disposal. Element 41 is fabricated from a foam-type material which is resilient, yet substantially rigid enough, such that the needle portion of a used I.V. needle assembly can be easily and securely inserted or "stuck" into the top of element 41 for transport to disposal, yet easily removed from the element at the disposal site. As here embodied, element 41 is dimensioned to accommodate the needle portions of at least four intravenous-type needle assemblies, the tubing connections (shown as 41b in FIG. 6) of which are engagable within the two pairs of engaging slots 14e, 14f formed in sidewalls 14c and 14d of the transport well. Preferably, element 41 is dimensioned to substantially the same height and length as the interior of transport well 14, and is generally narrower in width.

The interior of transport well 14 is adapted to properly position element 41 therewithin for use. According to the invention, the interior facing surfaces of sidewalls 14a and 14b are formed with projecting pairs of guide rails (42a, 42b and 42c, 42d, respectively) which are vertically disposed along the height of the sidewalls. The guide rails within each pair are spaced from each other on their respective sidewall surfaces a distance substantially equal to the width of element 41, such that the element can be slidably inserted and snugly retained between the guide rails. Additionally, guide rails 42a, 42c and 42b, 42d are spaced a predetermined distance inwardly from the interior facing surface of adjacent sidewalls 14d and 14c, respectively, such that element 41 can be inserted substantially in the middle of transport well 14 and not block any portion of the two pairs of engaging slots 14e, 14f. Advantageously, each guide rail is substantially narrower in width than the abutting sides of element 41 so that sufficient sidewall portions of element 41 will be exposed to permit easy removal of the element from the transport well for replacement.

To ensure that element 41 will be securely retained in transport well 14 while in use, the interior facing surfaces of sidewalls 14a and 14b are further formed with vertically disposed, projecting friction rails 43a and 43b, which are positioned between guide rail pairs 42a, 42b and 42c, 42d, respectively. As preferably embodied, the top edge of each friction rail is upwardly tapered like the edge of a knife blade such that when element 41 is inserted into transport well 14 between the guide rails, the top edges cause the friction rails to slidably imbed themselves into the sides of the element, thereby creating enough of a frictional resistance to avoid inadvertent pulling of the element out of the well in response to the removal of a used needle from the element at the disposal site. It should be understood, however, that the resistance provided by the friction rails should not be so great as to prevent easy removal of element 41 from the transport well for replacement.

It will be appreciated by those skilled in the art that while the foregoing represents the most preferred embodiment of the present invention with respect to transport means for used I.V. needle assemblies, it is not meant to exclude other embodiments which contemplate the spirit of the invention as disclosed herein. For example, although less preferred, the guide rails can be eliminated from transport well 14 and foam element 41 can be dimensioned to essentially the length and width of the interior of the well for slidable insertion therewithin. In this configuration, the height of element 41 will be reduced so as not to extend above the bottom of any of the engaging slots 14e and 14f, and thus, not impair the placement of the tubular connection of a used I.V. needle within any given slot.

It should be apparent from the foregoing that, in accordance with this most preferred embodiment of transport well 14, the transport well will no longer store syringes disassembled from used needle/syringe assemblies. Accordingly, and as preferably embodied, the storage/carrying device is provided with an open-ended, tubular container 45 adapted to store and carry used needle/syringe assemblies to disposal, in-tact, without having to disassemble the needles from the syringes.

As shown in FIG. 8, container 45 has a tubular sidewall 45a formed from a plastic material adapted for frictional engagement with extension well 22. The bottom of the container is preferably provided with a hard, hollow plastic plug 46 for enhanced structural stability, but can be fabricated as a single, tubular piece if desired. Container 45 (and thus extension transport well 22) can be dimensioned to accommodate any size needle/syringe assembly or a plurality thereof, and, preferably, should have an interior sidewall height such that the finger grips (shown as 48c) of the syringes (shown as 48b) are sufficiently exposed above the sidewall of the container to permit easy removal of a needle/syringe assembly for disposal, while reducing the risk of potentially contaminating contact with the interior of the sidewall. As preferably embodied, the container is dimensioned to an interior height of approximately 3 ½ inches and an interior diameter of approximately 1 ½ inches, which will safely and comfortably accommodate four 3 millileter syringes. For use with a 60 millileter syringe, the interior diameter of the container should preferably be approximately 1 ⅜ inches.

Advantageously, the interior of the container is provided with a needle engaging insert 47 into which the needle portions (shown as 48a) of used needle/syringe assemblies (shown as 48) can be tightly inserted As here embodied, insert 47 is dimensioned to essentially the interior diameter of the container and to a height of approximately one inch. Preferably, element 47 is fabricated from a sponge rubber or plastic-type material to ensure a tight engagement with the needle upon insertion thereinto. Further, insert 47 is permanently affixed within container 45 near the container floor, preferably via a hot glue-type compound, to ensure that the insert will not be inadvertently pulled out of the container in response to the removal of a needle therefrom.

In use, a needle/syringe assembly ready for disposal is placed in container 45 (which has been tightly inserted into extension well member 22) such that the exposed needle is tightly stuck through insert 47. The tubular sidewall of the container surrounds the body of the syringe with the fingergrips thereof exposed above the sidewall. Any residual blood or medication remaining in the needle can drain into and be absorbed by insert 47. Advantageously, because of the tight engagement between the needle and insert 47, and the relatively small area for movement of the syringe provided by the diameter of the container, the potential for the needle/syringe assembly to roll about the sidewall of the container during transport to disposal, and thus the attendant sense of uneasiness about transporting the device under such circumstances, will be substantially reduced. Further, the tight engagement of the needle with the material of insert 47 will substantially reduce the risk of the needle/syringe assembly falling out of the container in the event the container is inadvertently tipped over or dropped during use.

When the container is filled to capacity with used needle/syringe assemblies, it can be carried via storage/carrying device 1 to the disposal site. There, the used devices can be removed from the container and put in the disposal unit. The container can then be re-used for further procedures. Each container 45 should be reused until the gripping power of insert 47 is substantially reduced, and thereby, the risk of a used needle/syringe assembly falling out of the container substantially increased. However, it is preferred that each container be disposed of after a 2 to 3 week period to guard against a potential undue buildup of contamination within the container.

Advantageously, container 45 can also be used to transport to disposal multi-sample needles used in vacuum-tube blood collection procedures The typical vacuum-tube blood collection apparatus includes a multi-sample (two-way) needle threadably engagable with a tubular collection tube holder (e.g. the VACU-TAINER brand manufactured by B-D), and a vacuum-tube blood collector slidably insertable within the collection tube holder such that the rubber coated needle portion of the multi-sample needle disposed inside the collection tube holder is inserted into the collector tube.

After a blood sample has been drawn from a patient, the collection tube holder may be used repeatedly for further procedures. The multi-sample needle, however, must be disposed of. In a manner similar to the needle/syringe assemblies hereinbefore described, the needle/collection tube holder assembly can be inserted into container 45 such that the needle is securely embedded within needle engaging insert 47 for transport of the used needle to the disposal site.

The tight engagement between the multi-sample needle and insert 47, and the small area for movement of the collection tube holder provided by the diameter of the container, will substantially reduce the risk of the collection tube holder rolling about the sidewall of the container during transport. Additionally, and as noted above with respect to needle/syringe assemblies, the tight engagement of the used multi-sample needle with the material of insert 47 will substantially reduce the risk of the needle/collection tube holder assembly falling out of container 45 in the event the container is dropped or otherwise mishandled during use. At the disposal site, the needle is removed from the collection tube holder by the appropriate means and disgarded in the disposal unit.

Because of the disposable nature of both the needle and syringe portions of used needle/syringe assemblies, it will be apparent to those skilled in the art that container 45 may be used without insert 47. For such applications, the interior sidewall height of the container should preferably be approximately 6 ⅛ inches so as to cover the entire needle/syringe assembly and thereby reduce the potential rolling effect thereof during transport Any residual blood or medication in the needle will drain directly into the bottom of the container. Because of the forementioned potential contamination to the interior sidewall of the container, the container is simply inverted at the disposal site to allow the needle/syringe assembly to slide out into the disposal unit without further handling of the device by the user.

According to another aspect of the invention, container 45 can be adapted for use independent of storage/carrying device 10. As illustrated in FIG. 9A, container 45 as hereinbefore described is additionally provided with a metal insert 50 (shown as a metal nut) securely sandwiched via a hot-glue compound between the bottom of needle engaging insert 47 and the bottom of hollow plastic plug 46. Insert 50 should be of a sufficient weight to stabilize the container when placed on a flat surface so that the container will not tip over or lean when a used needle/syringe assembly or a needle/collection tube holder assembly is inserted thereinto. Preferably, insert 50 should weigh at least 1 ⅛ ounces, and should have a diameter essentially equal to the inside diameter of plug 46 so as to be snugly insertable therewithin. Advantageously, the added weight provided by insert 50 enables the user to place the container on a flat surface and insert the used implement thereinto quickly and easily with one hand, without fear that the container will tip over.

As shown in FIGS. 9b and 9c, container 45 is further provided with an elongated tubular sleeve 51 having an open end 51a and a closed end 51b. As here embodied, sleeve 51 can be slidably placed via open end 51a over outer sidewall 45a of the container at either end thereof, and is proportioned for a secure frictional engagement with the sidewall Thus, the sleeve can be fit over the top of container 45 to cover the exposed finger grip portions of the used needle/syringe assemblies (or exposed collection tube holder portion of a needle/collection tube holder assembly) inserted into the container, or fit over the bottom of the container to secure the sleeve to the container while in use. Moreover, sleeve 51 is preferably elongated to cover a substantial portion of the container when slidably placed over either end so as to substantially reduce the risk of the sleeve falling off the container during use, yet expose a small portion of the container which can be grasped by the user to hold the container in place and thereby facilitate removal of the sleeve from the container. It will be recognized by those skilled in the art that the sleeve may be easily and securely affixed to either end of the container by means other than frictional engagement, for example, via reciprocating threads formed on the interior of open end 51a of the sleeve and the exterior of sidewall 45a of the container.

In use, a nurse or medical technician who must give an injection or draw a blood sample from a patient will remove sleeve 51 from the top of container 45, slidably secure it over the bottom end of the container, and place the container on a nearby flat surface. After performing the procedure, the nurse or technician will simply place the used needle/syringe assembly or needle/collection tube holder assembly within container 45 such that the needle end is securely stuck into insert 47, and then remove sleeve 51 from the bottom of the container and secure it back over the top of the container to completely cover the used implement. The nurse can then simply place the container in a uniform pocket and further attend to the patient, as well as to other patients When container 45 is filled to capacity with used needle/syringe assemblies (or a needle/collection tube holder assembly), the nurse can carry it to the disposal site, remove the sleeve from the top of the container, slide it over the container bottom, and remove the used devices for disposal. The container can then be reused as hereinbefore described.

It should be understood that the foregoing is not meant to exclude other embodiments which facilitate the objects of this aspect of the present invention. For example, insert 50 can be fashioned from a ceramic magnetic material and the bottom of plug 46 opened to expose the magnet to metallic surfaces onto which the container may be placed. As such, the magnetic attraction between the metal surface and the magnet will enhance the upright stability of the container. (It will be recognized that this embodiment is less preferred for use with non-metallic surfaces because of the relatively light weight of the magnet). Further, a heavier plug 46 can be provided which will serve to eliminate insert 50 altogether.

It will be appreciated by those skilled in the art that container 45, as preferably embodied, is particularly advantageous for use with psychiatric patients, from whom it is desirable to keep all items with which the patient could potentially inflect injury upon himself or others in or about his room. Also, the upright stability of container 45 provided by the foregoing aspect of the present invention facilitates compliance with the C.D.C. recommendation that medical personnel do not hold any type of sheath device in one hand while attempting to insert a needle thereinto with the other hand. As described above, container 45, which can be construed as a sheath, can be accessed with one hand to insert a used needle/syringe assembly thereinto.

It will be further appreciated by those skilled in the art that the present invention in it broader aspects is not limited to the particular embodiments shown and described herein, and that variations may be made which are within the scope of the accompanying claims without departing from the principle of the invention and without sacrificing its chief advantages.

What is claimed is:

1. A hand-holdable, storage/carrying device for needle/syringe assemblies, comprising:
   a carrying handle;
   a first transport well, said first transport well attached along an upstanding sidewall portion thereof to one end of said carrying handle, said first transport well provided with a needle engaging element insertable therewithin, said needle engaging element being formed from a foam-type material adapted to receive and engage a plurality of intravenous-type needles insertable thereinto for transport to disposal;
   a second transport well, said second transport well being attached along an upstanding sidewall portion thereof to the other end of said carrying handle in generally opposed placement to said first transport well; and
   a pair of carrying trays disposed on opposite sides of said carrying handle, each of said pair of carrying trays being attached to both said first and second transport wells.

2. A storage/carrying device according to claim 1, which further comprises a generally U-shaped cylindrical extension transport well member, said extension well member formed integrally with said first transport well in generally opposed placement to said attaching sidewall portion thereof.

3. A storage/carrying device according to claim 1, wherein each of said pair of carrying trays comprises:
   a first upstanding sidewall connecting said first transport well and said second transport well so as to bridge the distance therebetween;
   a base portion extending outwardly from the lower edge of said first upstanding sidewall in perpendicular thereto; and
   a second upstanding sidewall, said second sidewall formed around the edges of said base portion which extend outwardly from said first upstanding sidewall.

4. A storage/carrying device according to claim 3, wherein one of said pair of carrying trays is provided with a retaining slot formed in said second sidewall thereof, said retaining slot proportioned so as to slidably receive and retain the handle of a pair of scissors placed in said one carrying tray such that the blades thereof rest along the length of said base portion.

5. A storage/carrying device according to claim 4, wherein each of said pair of carrying trays is proportioned to receive and retain two standard one-ounce medication cups.

6. A storage/carrying device according to claim 1, wherein said first transport well is provided with a plurality of engaging slots formed through the top edge of each of two opposing sidewall portions thereof, each of said plurality of engaging slots proportioned to receive and frictionally engage the plastic tubing attachment of an intravenous-type needle assembly.

7. A storage/carrying device according to claim 6, wherein said first transport well is proportioned to closely receive and securely retain a standard one-ounce medication cup into which the needle portions of said intravenous-type needle assemblies as well as the syringe portions of used needle/syringe assemblies can be safely placed and securely stored for transport to disposal.

8. A hand-holdable, storage/carrying device for needle/syringe assemblies, comprising:
   a carrying handle;
   a first transport well, said first transport well attached along an upstanding sidewall portion thereof to one end of said carrying handle, said first transport well being provided with a plurality of engaging slots formed through the top edge of each of two opposing sidewall portions thereof, each of said plurality of engaging slots proportioned to receive and frictionally engage the plastic tubing attachment of an intravenous-type needle assembly, said first transport well being further provided with a needle engaging element insertable therewithin, said needle engaging element being formed from a foam-type material adapted to receive and engage a plurality of intravenous-type needles insertable thereinto for transport to disposal;
   a second transport well, said second transport well being attached along an upstanding sidewall portion thereof to the other end of said carrying handle in generally opposed placement to said first transport well; and
   a pair of carrying trays disposed on opposite sides of said carrying handle, each of said pair of carrying trays being attached to both said first and second transport wells.

9. A storage/carrying device according to claim 8, wherein said first transport well is further provided with:
   a pair of projecting guide rails formed vertically on the interior surface of each of two opposed sidewall portions of said first transport well, said pairs of projecting guide rails adapted to slidably receive and retain said needle engaging element therebetween; and
   a friction rail formed on each of said opposed sidewall portions between the guide rails within each said pair, each said friction rail adapted to slidably imbed itself into a portion of said needle engaging element upon slidable insertion thereof between said pairs of guide rails so as to create enough of a frictional resistance to prevent said needle engaging element from being inadvertently pulled out of said first transport well in response to the removal of a needle inserted thereinto, while at the same time permitting easy removal of said needle engaging element from said first transport well for replacement.

10. A storage/carrying device according to claim 9, wherein said first transport well is formed in a generally square configuration.

11. A storage/carrying device according to claim 1, wherein said carrying handle comprises a grasping portion and a pair of opposed integral leg members extending downwardly therefrom, said grasping portion being disposed higher than said first and second transport wells and proportioned so as to substantially bridge the distance therebetween, one of said pair of leg members being formed integrally with said first transport well attaching sidewall portion, the second of said pair of leg members being formed integrally with said second transport well attaching sidewall portion.

12. A storage/carrying device according to claim 1 wherein said second transport well is formed in a generally U-shaped cylindrical configuration, said second transport well being adapted to securely retain therein a plurality of sterile needle/syringe assemblies such that the safety-capped needle portions thereof rest along the bottom of said second transport well.

13. A storage/carrying device according to claim 12, wherein said second transport well is proportioned to a depth generally 1.5 times greater than said first transport well.

14. A storage/carrying device according to claim 12, wherein said first transport well is proportioned to generally the same depth as said second transport well.

15. A storage/carrying device according to claim 2, wherein said extension well member is proportioned to generally the same depth as said first transport well.

16. A hand-holdable, storage/carrying device for needle/syringe assemblies, comprising:
 a carrying handle;
 a first transport well, said first transport well attached along an upstanding sidewall portion thereof to one end of said carrying handle;
 a second transport well, said second transport well being attached along an upstanding sidewall portion thereof to the other end of said carrying handle in generally opposed placement to said first transport well;
 a pair of carrying trays disposed on opposite sides of said carrying handle, each of said pair of carrying trays being attached to both said first and second transport wells; and
 a generally U-shaped cylindrical extension transport well member, said extension well member formed integrally with said first transport well in generally opposed placement to said attaching sidewall portion thereof, said extension well member provided with a re-usable tubular container frictionally insertable thereinto, said tubular container being open at the top end thereof and proportioned to retain a plurality of used needle/syringe assemblies therewithin for transport to disposal such that the syringe finger grips of said used needle/syringe assemblies are exposed sufficiently above the opening of said container to permit said finger grips to be grasped so as to remove said assemblies from said container substantially without risk of potential contaminating contact with said container, said container being formed with a needle engaging insert positioned at the bottom thereof, said needle engaging insert adapted to receive and engage the needle portion of said plurality of used needle/syringe assemblies so as to substantially reduce the potential for the syringe portions thereof to roll within said container during transport, while further reducing the risk of any of said used needle/syringe assemblies falling out of said container in the event said container is inadvertently dropped or inverted during use.

17. A storage/carrying device according to claim 16, wherein said container is further capable of retaining a multi-sample needle/collection tube holder assembly therein for transport of a used multi-sample needle to disposal, said collection tube holder being exposed sufficiently above the opening of said container to permit said collection tube holder to be grasped so as to remove said assembly from said container substantially without risk of potential contaminating contact with the interior sidewall of said container, said used multi-sample needle being fixedly inserted into said needle engaging insert so as to substantially reduce the potential for said collection tube holder to roll within said container during transport, while further reducing the risk of said assembly falling out of said container in the event said container is inadvertently dropped or inverted during use.

18. A hand-holdable, storage/carrying device for needle/syringe assemblies, comprising:
 a carrying handle;
 a first transport well, said first transport well attached along an upstanding sidewall portion thereof to one end of said carrying handle;
 a second transport well, said second transport well being attached along an upstanding sidewall portion thereof to the other end of said carrying handle in generally opposed placement to said first transport well;
 a pair of carrying trays disposed on opposite sides of said carrying handle, each of said pair of carrying trays being attached to both said first and second transport wells; and
 a generally U-shaped cylindrical extension transport well member, said extension well member formed integrally with said first transport well in generally opposed placement to said attaching sidewall portion thereof, said extension transport well provided with an open-ended tubular container frictionally insertable thereinto, said tubular container being proportioned to retain a plurality of used needle/syringe assemblies therewithin for transport to disposal such that the finger grips of said used needle/syringe assemblies are disposed below the opening of said container.

19. A storage/carrying device according to claim 1, wherein said device is integrally formed from an injection moldable, thermo-plastic material.

20. A hand-holdable, storage/carrying device for needle/syringe assemblies formed from an injection moldable, thermo-plastic material, comprising:
 a carrying handle;
 a generally square first transport well, said first transport well attached along a sidewall thereof to one end of said carrying handle, said first transport well provided with a needle engaging element insertable therewithin, said needle engaging element formed from a foam-type material adapted to receive and engage the needle portion of a plurality of intravenous-type needle assemblies insertable thereinto for transport to disposal;
 a second transport well having a flat sidewall and a generally U-shaped cylindrical sidewall formed integrally therewith, said second transport well attached to the other end of said carrying handle such that said flat sidewall faces said attaching sidewall of said first transport well, said second transport well being proportioned to securely retain therein a plurality of sterile needle/syringe assemblies such that the safety-capped needle ends thereof rest along the bottom of said second transport well;

a pair of carrying trays disposed on opposite sides of said carrying handle, each of said pair of carrying trays comprising a first upstanding sidewall connected to said attaching sidewall of said first transport well and to said flat sidewall of said second transport well so as to bridge the distance therebetween, a base portion extending outwardly from the lower edge of said first upstanding sidewall in perpendicular thereto, and a second upstanding sidewall formed around the edges of said base portion which extend outwardly from said first upstanding sidewall; and a generally U-shaped cylindrical extension transport well member, said extension well member formed integrally with the sidewall of said first transport well disposed opposite said attaching sidewall, said extension well member being adapted to store therewithin for transport to disposal a plurality of used needle/syringe assemblies.

21. A storage/carrying device according to claim 20, wherein one of said pair of carrying trays is provided with a retaining slot formed in said second sidewall thereof, said retaining slot proportioned to slidably receive and retain the handle of a pair of scissors placed in said one carrying tray such that the blades thereof rest along the length of said base portion.

22. A storage carrying/device according to claim 21, wherein each of said pair of carrying trays is proportioned to receive and retain two standard one-ounce medication cups.

23. A hand-holdable, storage/carrying device for needle/syringe assemblies formed from an injection moldable, thermo-plastic material, comprising:

a carrying handle;

a generally square first transport well, said first transport well attached along a sidewall thereof to one end of said carrying handle, said first transport well being adapted to securely store and transport to disposal a plurality of used intravenous-type needle assemblies, said first transport well provided with a plurality of engaging slots formed through the top edge of each of two opposing sidewall portions thereof, each of said plurality of engaging slots proportioned to receive and frictionally engage the plastic tubing attachment of one of said plurality of intravenous-type needle assemblies, said first transport well being further provided with a needle engaging element insertable therewithin, said needle engaging element formed from a foam-type material adapted to receive and engage the needle portion of each of said plurality of intravenous-type needle assemblies insertable thereinto for transport to disposal;

a second transport well having a flat sidewall and a generally U-shaped cylindrical sidewall formed integrally therewith, said second transport well attached to the other end of said carrying handle such that said flat sidewall faces said attaching sidewall of said first transport well, said second transport well being proportioned to securely retain therein a plurality of sterile needle/syringe assemblies such that the safety-capped needle ends thereof rest along the bottom of said second transport well;

a pair of carrying trays disposed on opposite sides of said carrying handle, each of said pair of carrying trays comprising a first upstanding sidewall connected to said attaching sidewall of said first transport well and to said flat sidewall of said second transport well so as to bridge the distance therebetween, a base portion extending outwardly from the lower edge of said first upstanding sidewall in perpendicular thereto, and a second upstanding sidewall formed around the edges of said base portion which extend outwardly from said first upstanding sidewall; and a generally U-shaped cylindrical extension transport well member, said extension well member formed integrally with the sidewall of said first transport well disposed opposite said attaching sidewall, said extension well member being adapted to store therewithin for transport to disposal a plurality of used needle/syringe assemblies.

24. A storage/carrying device according to claim 23, wherein said first transport well is further provided with:

a pair of projecting guide rails formed vertically on the interior surface of each of two opposed sidewall portions of said first transport well, said pairs of projecting guide rails adapted to slidably receive and retain said needle engaging element therebetween; and a friction rail formed on each of said opposed sidewall portions between each said pair of guide rails each said friction rail adapted to slidably imbed itself into a portion of said needle engaging element upon slidable insertion thereof between said pairs of guide rails so as to create enough of a frictional resistance to prevent said needle engaging element from being inadvertently pulled out of said first transport well in response to the removal of a needle inserted thereinto, while at the same time permitting easy removal of said needle engaging element from said first transport well for replacement 25. A storage/carrying device according to claim 20, wherein said carrying handle comprises a grasping portion and a pair of opposed integral leg members extending downwardly therefrom, said grasping portion being disposed higher than said first and second transport wells and proportioned so as to substantially bridge the distance therebetween, one of said pair of leg members being formed integrally with said attaching sidewall of said first transport well, the second of said pair of leg members being formed integrally with said flat sidewall of said second transport well 26. A storage/carrying device according to claim 20, wherein said second transport well is proportioned to a depth generally 1.5 times greater than said first transport well.

27. A storage/carrying device according to claim 20, wherein said extension well member is proportioned to generally the same depth as said first transport well 28. A storage/carrying device according to claim 24, wherein said extension well member is provided with a re-usable tubular container frictionally insertable thereinto, said tubular container being open at the top end thereof and proportioned to retain said plurality of used needle/syringe assemblies therewithin for transport to disposal such that the syringe finger grips of said used needle/syringe assemblies are exposed sufficiently above the opening of said container to permit said finger grips to be grasped so as to remove said assemblies from said container substantially without risk of potential contaminating contact with the interior sidewall of said container, said container being formed with a needle engaging insert fixedly positioned at the bottom thereof, said needle engaging insert adapted to receive and fixedly engage the needle portions of said plurality of used needle/syringe assemblies so as to substantially reduce the potential for the syringe portions thereof to roll within said container during transport, while further reducing the risk of any of said used needle/syringe assemblies falling out of said container in the event said container is inadvertently dropped or inverted during use.

29. A storage/carrying device according to claim 28, wherein said container is further capable of retaining a multi-sample needle/collection tube holder assembly therein for transport of a used multi-sample needle to disposal, said collection tube holder being exposed sufficiently above the opening of said container to permit said collection tube holder to be grasped so as to remove said assembly from said container substantially without risk of potential contaminating contact with the interior sidewall of said container, said used multi-sample needle being fixedly inserted into said needle engaging insert so as to substantially reduce the potential for said collection tube holder to roll within said container during transport, while further reducing the risk of said assembly falling out of said container in the event said container is inadvertently dropped or inverted during use.

* * * * *